(12) United States Patent
Puskas et al.

(10) Patent No.: US 6,747,098 B2
(45) Date of Patent: Jun. 8, 2004

(54) ARBORESCENT THERMOPLASTIC ELASTOMERS AND PRODUCTS THEREFROM

(75) Inventors: Judit E. Puskas, London (CA); Christophe Paulo, Lyons (FR); Prince Antony, London (CA)

(73) Assignee: The University of Western Ontario, London (CA)

( * ) Notice: Subject to any disclaimer, the term of this patent is extended or adjusted under 35 U.S.C. 154(b) by 22 days.

(21) Appl. No.: 10/156,767

(22) Filed: May 29, 2002

(65) Prior Publication Data

US 2003/0065098 A1 Apr. 3, 2003

Related U.S. Application Data

(60) Provisional application No. 60/293,508, filed on May 29, 2001.

(51) Int. Cl.$^7$ .......................... C08L 53/00; C08G 83/00
(52) U.S. Cl. .................. 525/314; 525/244; 525/245; 525/268; 525/98; 525/316
(58) Field of Search ................................ 525/314, 316, 525/244, 245, 268, 98, 937, 938

(56) References Cited

U.S. PATENT DOCUMENTS

| | | |
|---|---|---|
| 4,946,899 A | 8/1990 | Kennedy |
| RE34,640 E | 6/1994 | Kennedy |
| 5,395,885 A | 3/1995 | Kennedy |
| 5,428,111 A | 6/1995 | Faust |
| 5,458,796 A | 10/1995 | Storey |
| 5,630,844 A | 5/1997 | Dogan |
| 5,721,331 A | 2/1998 | Shachi |
| 5,741,331 A | 4/1998 | Pinchuk |
| 6,102,939 A | 8/2000 | Pinchuk |
| 6,156,859 A | 12/2000 | Langstein |
| 6,197,240 B1 | 3/2001 | Pinchuk |

FOREIGN PATENT DOCUMENTS

| | | |
|---|---|---|
| WO | 0232982 | 4/2002 |

OTHER PUBLICATIONS

Pinchuk, L.; Khan I.J.; Martin, J.B.; Bridgeman, J.; Wilson, G.J.; Glass, J.; Si, J.; Kennedy, J.P.; "A New Family of Thermoplastic Elastomers for Ultra–Long Term Implant Based Upon a Backbone of Alternating Quaternary and Secondary Carbons"; 24th Annual Meeting of the Society for Biomaterials; San Diego, CA, Apr. 22–26, 1998, p. 173.
Pinchuk, L.; Khan, I.J.; Martin, J.B.; Wilson, Martin and G.J.; "Polyisobutylene–Based Thermoplastic Elastomers For Ultra Long–Term Implant Applications", Society for Biomaterials, 2000, p. 1452.
"Nonlinear rheology of hyperbranched polyisobutylene", Robertson et al., J. Rheol. 46(1), pp. 307–320, Jan./Feb. (2002).
"Uniform Highly Branched Polymers by Anionic Grafting: Arborescent Graft Polymers", Gauthier et al., Macromolecules 1991, 24, pp. 4548–4553.
"Linear viscoelastic properties of Hyper branched polyisobutylene", Robertson et al., J. Rheol. 45(3), pp. 759–772, (2001).
"Rheology of Star–Branched Polyisobutylene", Santangelo et al., Macromolecules 1999, 32, pp. 1972–1977.
Puskas, J.E. et al., "Star–Branched and Hyperbranched Polyisobutylenes", Macromolecular Symposia, Wiley VCH, Weinheim, DE, vol. 132, Jul. 1998, pp. 117–126, XP000790730, ISSN: 1022–1360.

*Primary Examiner*—James J. Seidleck
*Assistant Examiner*—Olga Asinovsky
(74) *Attorney, Agent, or Firm*—Lynn C. Schumacher; Hill & Schumacher (57) ABSTRACT

The present invention provides highly branched block copolymers comprising branched soft segments with a low glass-transition temperature ($T_g$) and hard segments with a high $T_g$ or crystalline melting point that exhibit thermoplastic elastomeric properties. More particularly the invention provides a highly branched block copolymer of a polyisoolefin and a polymonovinylidene arene characterized by having thermoplastic elastomeric properties wherein the aforesaid block copolymer comprises a highly branched polyisoolefin block and some of the branches of the aforesaid polyisoolefin block terminate in polymonovinylidene arene endblocks.

72 Claims, 7 Drawing Sheets

First generation

PS    PIB

Linear triblock

PRIOR ART

FIGURE 1A

Triarm-star block

PRIOR ART

FIGURE 1B

PRIOR ART

FIGURE 1C

Multiarm-star block

PRIOR ART

R = methyl
2,3,5,6-tetramethyl-
4-(2-hydoxyisopropyl)styrene 3-(2-methoxyisopropyl)
styrene 4-(epoxyisopropyl)styrene n = 1

4,4,6-trimethyl-6-hydroxyl-1-heptene 4,4,6-trimethyl-6-chloro-1-heptene 4,4,6-trimethyl-6,7-epoxy-1-heptene n = 2

4,4,6,6,8-pentamethyl-8-hydroxyl-1-nonene

4,4,6,6,8-pentamethyl-8-chloro-1-nonene

4,4,6,6,8-pentamethyl-8,9-epoxy-1-nonene

FIGURE 5 (continued)

$R_1, R_3 \longrightarrow$ H, alkyl, aryl $R_2 \longrightarrow$ X halide (Cl, Br, F, I)

ester ether

B:  epoxide: $R_4$ : H, alkyl, aryl

FIGURE 5 (continued)

ARBORESCENT THERMOPLASTIC ELASTOMERS AND PRODUCTS THEREFROM

CROSS REFERENCE TO RELATED U.S. PATENT APPLICATIONS

This patent application relates to U.S. provisional patent application Serial No. 60/293,508 filed on May 29, 2001 now abandoned entitled NOVEL ARBORESCENT (HYPERBRANCHED OR RANDOMLY BRANCHED) THERMOPLASTIC ELASTOMERS.

FIELD OF THE INVENTION

This invention relates to arborescent or highly branched block copolymers comprising branched soft segments with a low glass-transition temperature ($T_g$) and hard segments with a high $T_g$ or crystalline melting point that exhibit thermoplastic elastomeric properties. More particularly this invention relates to highly branched block copolymers of polyisoolefins and polymonovinylidene arenes that exhibit thermoplastic elastomeric properties.

BACKGROUND OF THE INVENTION

Thermoplastic elastomers (TPEs) are polymeric materials, which combine the properties of vulcanized rubbers and the processability and recylability of thermoplastics, see for example B. M. Walker, "Handbook of Thermoplastic Elastomers", Van Nostrand Reinhold, New York (1979). While blends of elastomers and plastics are not compatible and show gross phase separation, block copolymers can only phase separate on a microscopic scale due to the connectivity of elastomeric and plastic blocks.

Branched polymers are of commercial interest due to their having markedly lower viscosity and less shear sensitivity than their linear counterparts. Thus branched block copolymers that have the added benefit of being thermoplastic elastomers should have a wide variety of commercial applications depending upon the elastomer and the thermoplastic used to form the block copolymer.

About 40% of TPEs are block copolymers, which contain both soft segments with a low glass-transition temperature ($T_g$) and hard segments with a high $T_g$ or crystalline melting point, see G. Holden, in "Rubber Technology", ed. M. Morton, Van Nostrand Reinhold, New York, Ch. 16, 465 (1987). The hard segments associate, leading to physical crosslinks, which disappear when heated above a certain temperature (Order-Disorder Temperature, ODT) and reappear immediately on cooling. The hard phase determines the mechanical strength, heat resistance, upper service temperature and strongly affects the oil and solvent resistance of a TPE. The chemical nature of the soft segments has an influence on elastic behavior, low temperature flexibility, thermal stability and aging resistance. According to present understanding in the field, in order to get good phase separation in block-type TPEs leading to good mechanical properties, the length of the elastomer chains should be as uniform as possible. This can be achieved by living polymerization, a unique process without termination and other side reactions of the growing polymer chain. Living conditions producing relatively uniform polymers can be achieved in anionic, cationic and radical systems.

An important commercial example of thermoplastic elastomeric block copolymers is styrene-elastomer-styrene, produced by living anionic polymerization. Most of the styrenic block copolymers have the general formula S-E-S, where S represents a hard amorphous polystyrene block and E represents a soft elastomeric block. Many of the polystyrene-polydiene block copolymers that are TPEs have the basic structure poly(styrene-block-butadiene-block-styrene) (S-B-S) or poly(styrene-block-isoprene-block-styrene) (S-I-S). The applications of these block copolymers are numerous. Important applications include solvent based and hot melt adhesives, sealants, coatings, hose, asphalt modifiers and sporting goods and automobiles, see G. Holden, N. R. Legge, R. Quirk, H. E. Schroeder (Eds.), "Thermoplastic Elastomers—A comprehensive Review", Hanser Publishers, Munich (1996) and G. Holden, in "Encyclopedia of Polymer Science and Engineering", ed. J. I. Kroschwitz, John Wiley and Sons, New York, Vol. 5, 416 (1996).

Figure 1A:
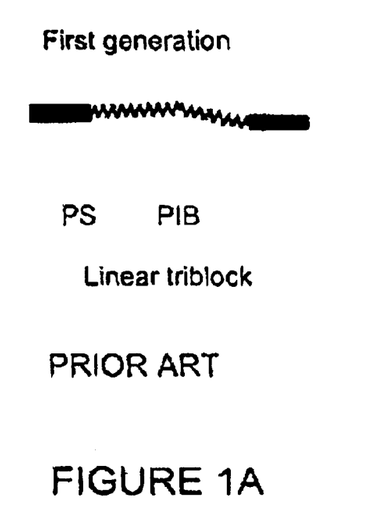
FIG. 1A shows a diagrammatic representation of PRIOR ART first generation linear triblock polyisobutylene-polystyrene (PIB-PS) block-type thermoplastic elastomers (TPEs)
Figure 1B:
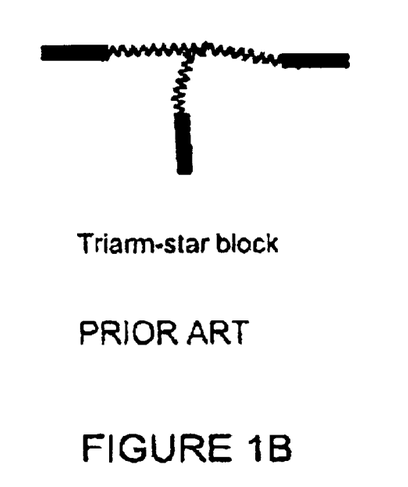
FIG. 1B shows a diagrammatic representation of PRIOR ART first generation triarm-star block polyisobutylene-polystyrene (PIB-PS) block-type thermoplastic elastomers (TPEs)
Figure 1C:
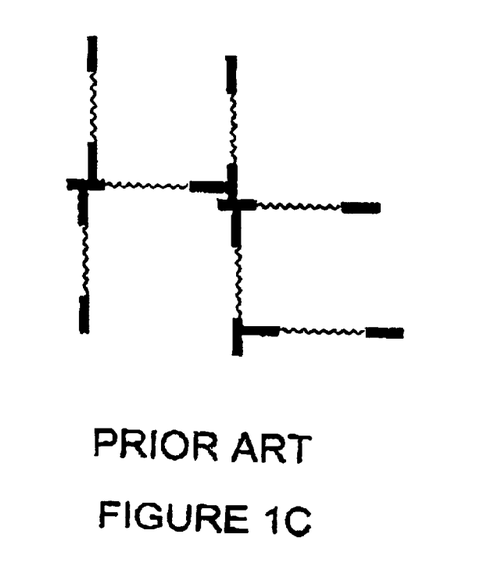
FIG. 1C shows a diagram of the structure of PRIOR ART PIB-PS multiblock copolymers disclosed in U.S. Pat. No. 5,721,331.

Recently, TPEs from another class of styrenic block copolymers have been developed with polyisobutylene (PIB) elastomeric segments, see U.S. Pat. No. 4,946,899 issued to J. P. Kennedy et al. FIGS. 1A and 1B show a diagrammatic representation of the first generation of these PIB-based TPEs which are linear triblock (FIG. 1A) and triarm—star block structures shown in FIG. 1b. An important advantage of these TPEs based on polyisobutylene-polystyrene (S-IB-S) block copolymers is that there is no need of hydrogenation of the elastomeric segments like that in the case of S-B-S or S-I-S, because of the presence of a saturated PIB elastomeric block. These novel TPEs were found to have excellent damping characteristics (similar to butyl rubber over a wide frequency range), oxidative and hydrolytic stability and good gas barrier properties, see K. Koshimura, H. Sato, Polym. Bull, 29, 705 (1992) and J. P. Puskas, G. Kaszas, Rubber Chem. Technol., 66, 462 (1996).

The first generation of these TPEs were linear and triarm-star blocks, whose synthesis and basic chemical characterization have been reported, see G. Kaszas, J. E. Puskas, W. G. Hager and J. P. Kennedy, J. Polym. Sci., Polym. Chem., A29, 427 (1991).and J. E. Puskas, G. Kaszas, J. P. Kennedy, W. G. Hager, J. Polym. Sci., Polym. Chem., A30, 41 (1992). The living polymerization of IB by di- and tri-functional initiators gives a uniform rubbery mid-block, followed by the sequential addition of styrene (St) which results in a glassy outer block.

The architecture of copolymers can be controlled by the synthesis procedure, and TPEs with various composition and molecular weight (MW) have been prepared and characterized; for a review see J. P. Puskas, G. Kaszas, Rubber Chem. Technol., 66, 462 (1996). The most frequently used initiators are di- and tricumyl derivatives, especially di- and tricumyl-ether and -chloride. The co-initiator mainly used for making high molecular weight PIBs, suitable for block copolymer synthesis, is $TiCl_4$. The control of living IB polymerization is further improved by the use of electron pair donors like dimethyl sulfoxide or dimethyl acetamide and a proton trap such as di-tert-butyl pyridine (DtBP). These additives lead to better control of IB polymerization, resulting in narrow molecular weight distribution (MWD) PIB, and also improve the blocking efficiency of St monomers during TPE synthesis.

The S-IB-S triblocks and three-arm radial blocks obtained in the absence of electron pair donor and/or proton trap exhibit poor tensile properties due to inefficient blocking. The process has successfully been scaled up to a lb/batch scale (G. Kaszas, Polym. Mater. Sci. Eng., 67, 325 (1992) and an inventory of block copolymers have been prepared and characterized (P. Antony, J. E. Puskas: Proceedings of the Polymer Processing Society Meeting, May 21–24, Montreal, Canada (2001). Kuraray Inc., Japan, recently test-marketed linear S-IB-S block copolymers. The important emerging applications of these first generation linear and tri-star block copolymer materials include medical applications such as rubber stoppers for drugs and blood, gaskets and caps for syringes, blood and drug storage bags and tubes and the like as disclosed in Japanese Patent No. 5,212,104; Japanese Patent No. 5,269,201; and Japanese Patent No. 5,295,054.

Due to the high oxidative and chemical stability of the S-IB-S macromolecules, these materials have the potential to replace silicone rubber or other soft to semirigid bio-implantable polymers; U.S. Pat. Nos. 5,741,331 (1998); 6,102,939 (2000); and 6,197,240 (2001) issued to Pinchuk, L. Pinchuk, I. J. Khan, J. B. Martin and G. J. Wilson: Polyisobutylene-Based Thermoplastic Elastomers For Ultra Long Term Implant Applications; Sixth World Biomaterials Congress Transactions, 1452 (2001), and Pinchuk, L., Khan, I. J., Martin, J. B., Bridgeman, J., Wilson, G. J., Glass, J., Si, J. and Kennedy, J. P.; A New Family of Thermoplastic Elastomers for Ultra-Long Term Implant Based Upon a Backbone of Alternating Quaternary and Secondary Carbons"; 24$^{th}$ Annual Meeting of the Society for Biomaterials; April 22–26, San Diego, (1998), p. 173; are directed to biologically stable, non-biodegradable implant devices and methods of producing same, using linear or star polyolefin copolymers having the structures shown in FIG. 1. They also disclosed the structure shown in FIG. 2A.

Figure 2A:
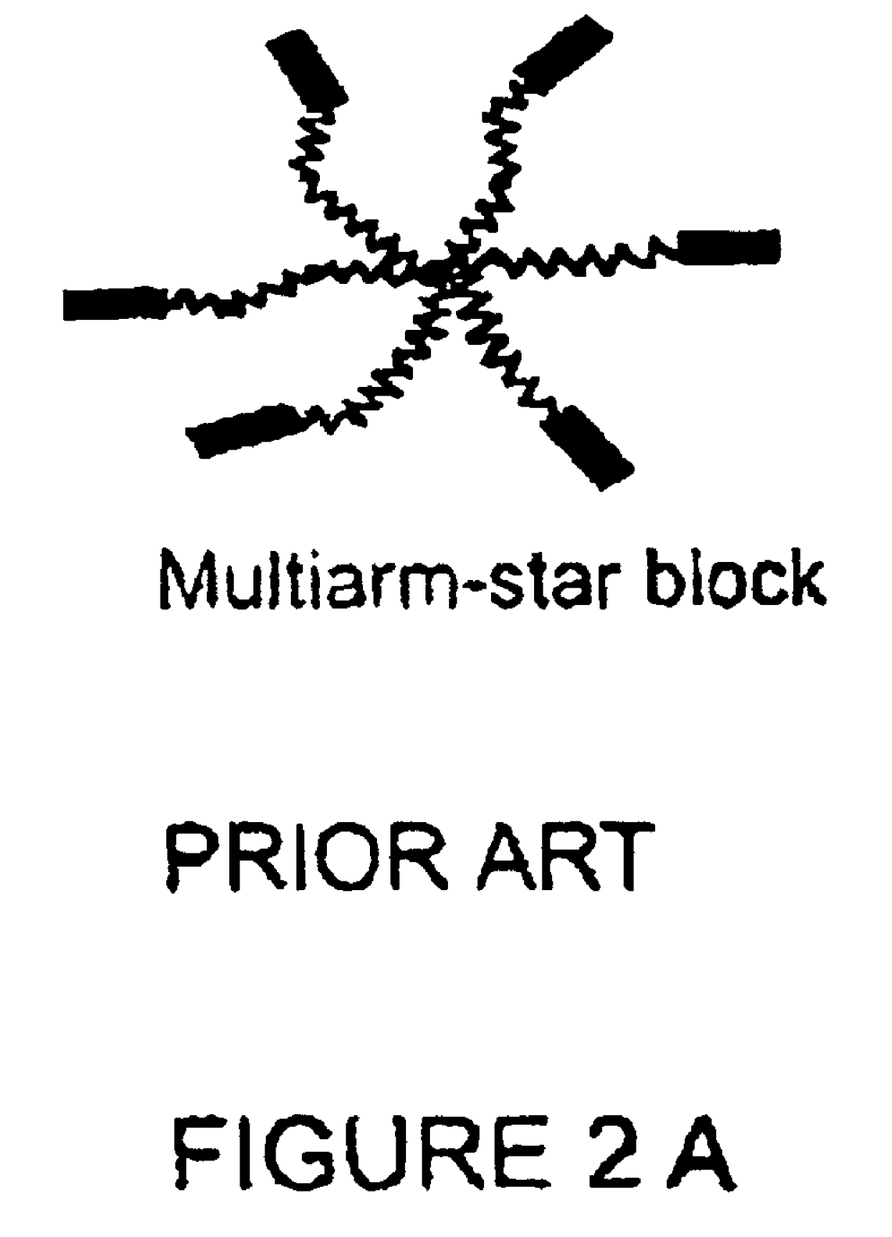
FIG. 2A shows a diagrammatic representation of PRIOR ART second generation multiarm-star block polyisobutylene-polystyrene (PIB-PS) block-type thermoplastic elastomers (TPEs)

The second generation of PIB-based TPEs shown in FIG. 2A are an even more recent development and include multi-arm-star blocks (S. Jacob, J. P. Kennedy, Advances in Polym. Sci, 146, 1 (1999); J. E. Puskas, W. Pattern, P. M. Wetmore, V. Krukonis, Rubber Chem. Technol. 72, 559 (1998). Multiarm-stars are expected to have improved strength and shear stability. Three-arm stars were shown to have considerably higher strength than comparable linear triblocks, but their shear sensitivity is still a concern; shearing off an arm would lead to a linear triblock. For polymers prepared by anionic polymerization beyond six arms no change in properties was found (L. K. Bi, L. J. Fetters, G. Quack, R. N. Young "The Synthesis, Rheology and Morphology of Star Block Copolymers", Rubbercon 77, Int. Rubber Conf., Akron, Ohio, Paper No. 11, 11 (1977).

Although there are several reports on the synthesis and characterization of linear triblock, three-, six-, octa- and multi-arm (10–60) star S-IB-S block copolymers in the literature, the effect of hard and soft segment composition and molecular architecture on the mechanical properties of these TPEs has not been studied systematically. It has been reported that the minimum PS molecular weight required for good phase separation and physical properties is around 8000, and the maximum tensile strength achieved was 17–24 MPa with 400–600 % elongation, depending on the measurement method (for reviews see J. P. Puskas, G. Kaszas, Rubber Chem. Technol., 66, 462 (1996) and J. E. Puskas, G. Kaszas, Progr. Polym. Sci., Elsevier Science Ltd., 25(3), 403 (2000)).

Referring again to U.S. Pat. No. 4,946,899, this patent discloses a thermoplastic elastomeric star-shaped block copolymer comprising a polyisobutylene midblock and endblocks of polymerized styrene wherein the ratio of the the weight average molecular weight to the number average molecular weight of the midblock is from about 1.01 to about 1.5. It is further disclosed that each branch of the aforesaid star-shaped block copolymer is of essentially equal length.

U.S. Pat. No. 5,428,111 issued to Faust et al. discloses a method of producing block copolymers having polyolefin midblocks and styrenic end blocks by the living polymerization of aromatic styrenic monomers initiated from living polyisoolefin chain end.

U.S. Pat. No. 5,458,796 issued to Storey et al. discloses a process for the synthesis of star polymers, specifically polyisobutylene star-branched polymers by living carbocationic polymerization of isobutylene homopolymers, random copolymers or block copolymers using a monofunctional initiator and subsequently linking the preformed arms using divinylbenzene or diisopropenylbenzene.

U.S. Pat. No. 5,721,331 issued to Shachi et al. is directed to a process of producing isobutylene-based block copolymers composed of isobutylene units and styrene blocks. This patent discloses that, if one uses the process disclosed in U.S. Pat. No. 4,946,899 issued to J. P. Kennedy et al., and continues the polymerization after the styrene monomer is consumed, the active living chain ends can attack the styrene block of another chain, creating multiblocks shown in FIG. 1C. This reaction, coupling via electrophilic substitution on the aromatic rings of the PS blocks, is well-known (Fodor Zs, Gyor M, Wang HC, Faust R. J Macromol Sci, Pure Appl Chem A 1993;30(5):349–63). Shachi claimed that this chain coupling, evidenced by multimodal molecular weight distribution (termed as "continuous distribution" in U.S. Pat. No. 5,721,331 where the GPC peaks correspond to multiplets of the Mn of the starting linear triblock material), leads to improved properties, namely higher tensile strength and lower tensile set values. Similar multiblocks, consisting of polyisobutylene rubbery segments and cyclized polyisoprene hard segments and exhibiting thermoplastic elastomeric properties, are disclosed in U.S. Pat. No. 4,910,261 issued to G. Kaszas, J. E. Puskas and J. P. Kennedy. These materials are a mixture of linear chains and various multiblocks. In the aforementioned two patents the polyisobutylene rubbery blocks are linear. The branched structure of the materials is the result of branching of the outer plastic blocks of the TPE.

Kee and Gauthier in Macromolecules, 32, 6478 et seq. (1999) describe the preparation of highly branched polystyrene-polyisoprene copolymers by the successive grafting of the polymeric building blocks (graft on graft) which have a well-defined structure and the average molecular weight distributions of both the highly branched polystyrene and the polystyrene-polyisoprene graft copolymer are very narrow, being 1.1 or less. U.S. Pat. No. 6,156,859 issued to Langstein et al. discloses a process for producing highly branched polyisoolefins by the reaction of isoolefins by polymerizing an isoolefin in the presence of a multfunctional monomer and an alkylalumoxane at a temperature between 20° C. and −100° C.

Puskas et al. reported the synthesis and characterization of arborescent polyisobutylenes by copolymerising an inimer with isobutylene (Makromol. Chem, Macromol. Symp. 132, 117 (1998); Proceedings of the World Polymer Congress (IUPAC Macro 2000), 384 (2000)). Arborescent (hyperbranched) polymers belong to the class of dendritic polymers but are characterized by an irregular tree-like structure. These polymers are a relatively recent development and very little structure-property relationship data is available, see D. A. Tomalia: Makromol. Chem., Macromol. Symp. 101, 243 (1996).

Heretofore there has not been disclosed an arborescent branched block copolymer with thermoplastic elastomeric properties comprising a highly branched polyisoolefin block wherein the branches are of irregular length in which some of the branches of the aforesaid polyisoolefin bear rigid polymer end block segments. Thus, it would be very advantageous to provide such materials that have thermoplastic elastomeric properties comparable, or superior, to the materials shown in FIG. 2A but which can be produced more economically than these materials. Such materials would have many uses including use as implantable prostheses in medical applications.

SUMMARY OF THE INVENTION

The present invention provides an arborescent branched block copolymer, comprising an arborescent elastomeric polymer block having more than one branching point, the arborescent elastomeric polymer block having a low glass-transition temperature ($T_g$), and some or all of the branches of the arborescent elastomeric polymer block being terminated in rigid polymer block segments with a high $T_g$ or crystalline melting point, the arborescent branched block copolymer exhibiting thermoplastic elastomeric properties.

The present invention also provides an arborescent branched block copolymer of a polyisoolefin and a polymonovinylidene arene comprising an arborescent elastomeric polyisoolefin polymer block having more than one branching point, and some or all of the branches of the aforesaid arborescent polyisoolefin polymer block terminate in polymonovinylidene arene plastic endblocks, the arborescent branched block copolymer having thermoplastic elastomeric properties.

The present invention also provides an arborescent branched block copolymer of polyisobutylene and polystyrene comprising an arborescent elastomeric polyisobutylene polymer block having more than one branching point and some or all of the branches of the aforesaid arborescent polyisobutylene polymer block being terminated with polystyrene endblocks, the arborescent branched block copolymer having thermoplastic elastomeric properties.

The present invention also provides a process for producing an arborescent branched block copolymer of a polyisoolefin and a polymonovinylidene arene, comprising:

a) polymerizing an isoolefin in the presence of at least one inimer and a Lewis acid halide coinitiator, at a temperature of between about −20° C. and −100° C. to produce an arborescent elastomeric branched polyisoolefin polymer having more than one branching point, the inimer including at least one group for (co)polymerizing in a cationic polymerization of the isoolefin and at least one group for initiating cationic polymerization of the isoolefin; and thereafter b) adding a compound having an effective electron pair donor for improving blocking efficiency and adding a monovinylidene arene suitable for the production of the polyvinylidene plastic blocks with some or all of the branches of the aforesaid arborescent elastomeric branched polyisoolefin polymer being terminated with polymonovinylidene arene plastic endblocks; and c) terminating said polymerization reaction after a selected period of time by addition of an effective nucleophile compound which terminates said polymerization reaction, said selected period of time being sufficiently long enough to ensure production of at least individual units of said arborescent branched block copolymer, the arborescent branched block copolymer of a polyisoolefin and a polymonovinylidene arene having thermoplastic elastomeric properties.

In the process the inimer, a compound carrying both an initiator and a monomer functionality (IM), is copolymerized with one or more olefins. Very high MW arborescent PIBs are produced using 4-(2-hydroxy-isopropyl) styrene and 4-(2-methoxy-isopropyl) styrene as IM in a "one-pot" living-type polymerization system. The reactive chain ends of arborescent PIB are blocked with a material such as stryrene to form PIB-PS blocks.

In another aspect of the invention there is provided a process for producing an arborescent branched polyisoolefin block copolymer, comprising:

a) polymerizing an isoolefin in the presence of an inimer and a Lewis acid halide coinitiator at a temperature of between about −20° C. and −100° C. to produce an elastomeric arborescent branched polyisoolefin polymer having more than one branching point, the the inimer having a formula where R can be H, $OH_3$ or an alkyl or aryl group; thereafter b) adding a compound having an effective electron pair donor for improving blocking efficiency and adding a monovinylidene arene suitable for the production of the polyvinylidene arene plastic endblocks; and c) terminating said polymerization reaction after a selected period of time by addition of an effective nucleophile compound which terminates said polymerization reaction, said selected period of time being sufficiently long enough to ensure production of at least individual units of said elastomeric arborescent branched block copolymer with some or all of the branches of the aforesaid elastomeric arborescent polyisoolefin polymer block terminated in polymonovinylidene arene plastic endblocks, the arborescent branched block copolymer having thermoplastic elastomeric properties.

The present invention also provides an arborescent branched block copolymer comprising an arborescent elastomeric polymer block having more than one branching point, the arborescent elastomeric polymer block having a low glass-transition temperature ($T_g$), and some or all of the branches of the arborescent elastomeric polymer block being terminated in rigid polymer block segments with a high $T_g$ or crystalline melting point the arborescent branched block copolymer exhibiting thermoplastic elastomeric properties formed into an article of manufacture comprising an implantable prosthesis or implant.

BRIEF DESCRIPTION OF THE DRAWINGS

The present invention will now be described by way of example only, reference being had to the accompanying drawings in which.

DETAILED DESCRIPTION OF THE INVENTION

Figure 4:
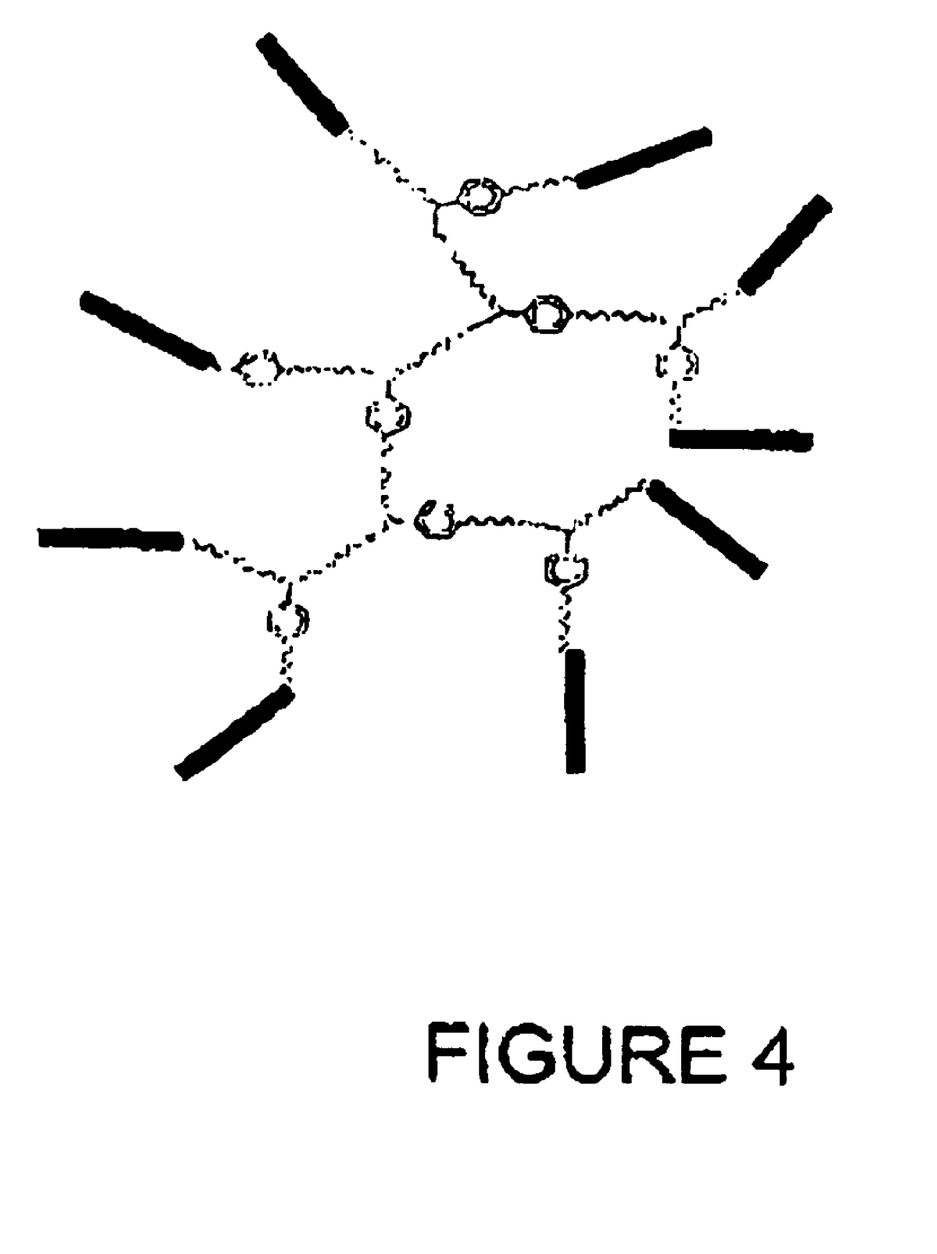
FIG. 4 shows a diagrammatic representation of a highly branched block copolymer produced according to the process illustrated in FIG. 3 comprising soft segments with a low glass-transition temperature ($T_g$) and hard segments with a high $T_g$ or crystalline melting point that exhibit thermoplastic elastomeric properties produced in accordance with the present invention.

Referring to FIG. 4, the present invention provides highly branched block copolymers comprising soft elastomeric segments with a low glass-transition temperature ($T_g$) and hard thermoplastic segments with a high $T_g$ or crystalline melting point so that the entire structure exhibits thermoplastic elastomeric properties.

The present invention provides in a preferred embodiment of the invention a highly branched block copolymer of a polyisoolefin and a polymonovinylidene arene characterized by having thermoplastic elastomeric properties wherein the aforesaid block copolymer comprises a highly branched polyisoolefin block and some of the branches of the aforesaid polyisoolefin block terminate in polymonovinylidene arene endblocks. In addition to the term "highly branched", the terms "arborescent" and "hyperbranched" also may be used to describe the structure disclosed herein. The highly branched or arborescent polymers have an irregular tree-like structure.

Figure 3:
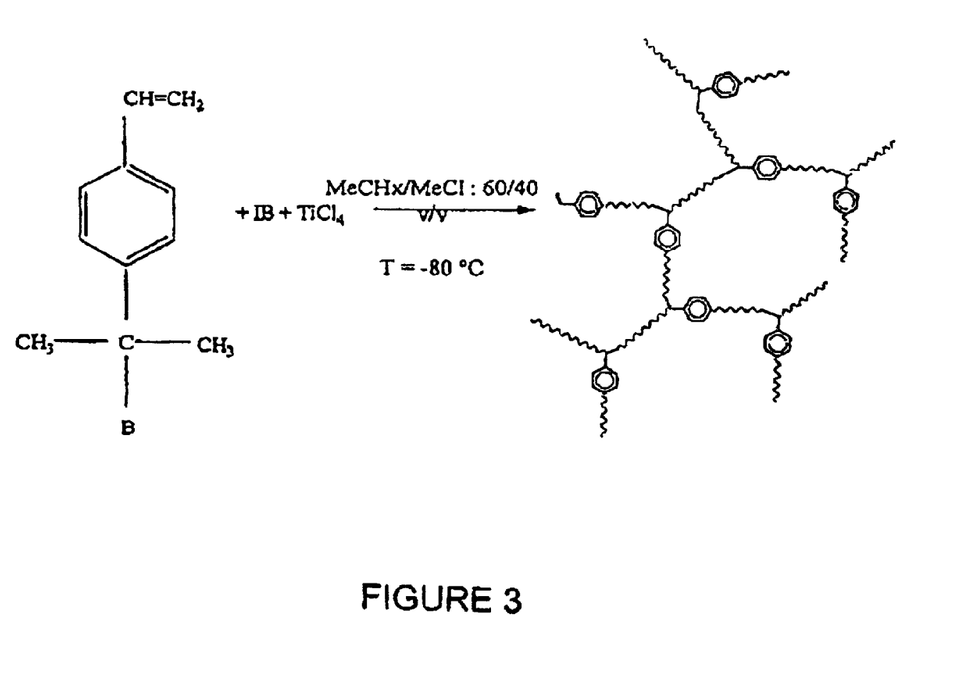
FIG. 3 shows an example reaction to produce the elastomeric midblock section of the highly branched block copolymers of the present invention.

The highly branched block copolymers of the present invention which have been found to exhibit thermoplastic elastomeric properties contain a highly branched polyisoolefin midblock that is synthesized using a process which involves use of an amount of inimer, a compound carrying both an initiator and a monomer functionality (IM), which is copolymerized with an olefin. Referring to FIG. 3, the inimers used in the present invention to initiate the polymerization and to introduce the random branching points into the elastomeric midblock can be represented by the general formula A-B, where A is a polymerizable function such as a vinylic double bond shown in FIG. 3 and B is an initiating group. For isobutylene polymerization B can be a tertiary ether, tertiary chloride, tertiary methoxy group or tertiary ester, well-known initiators for isobutylene polymerization. Very high MW arborescent PIBs were successfully synthesized by this method using 4-(2-hydroxy-isopropyl) styrene and 4-(2-methoxy-isopropyl) styrene as IM in a "one-pot" living-type polymerization system. The reactive chain ends of arborescent PIB have been blocked with St to form PIB-PS blocks.

Figure 5:
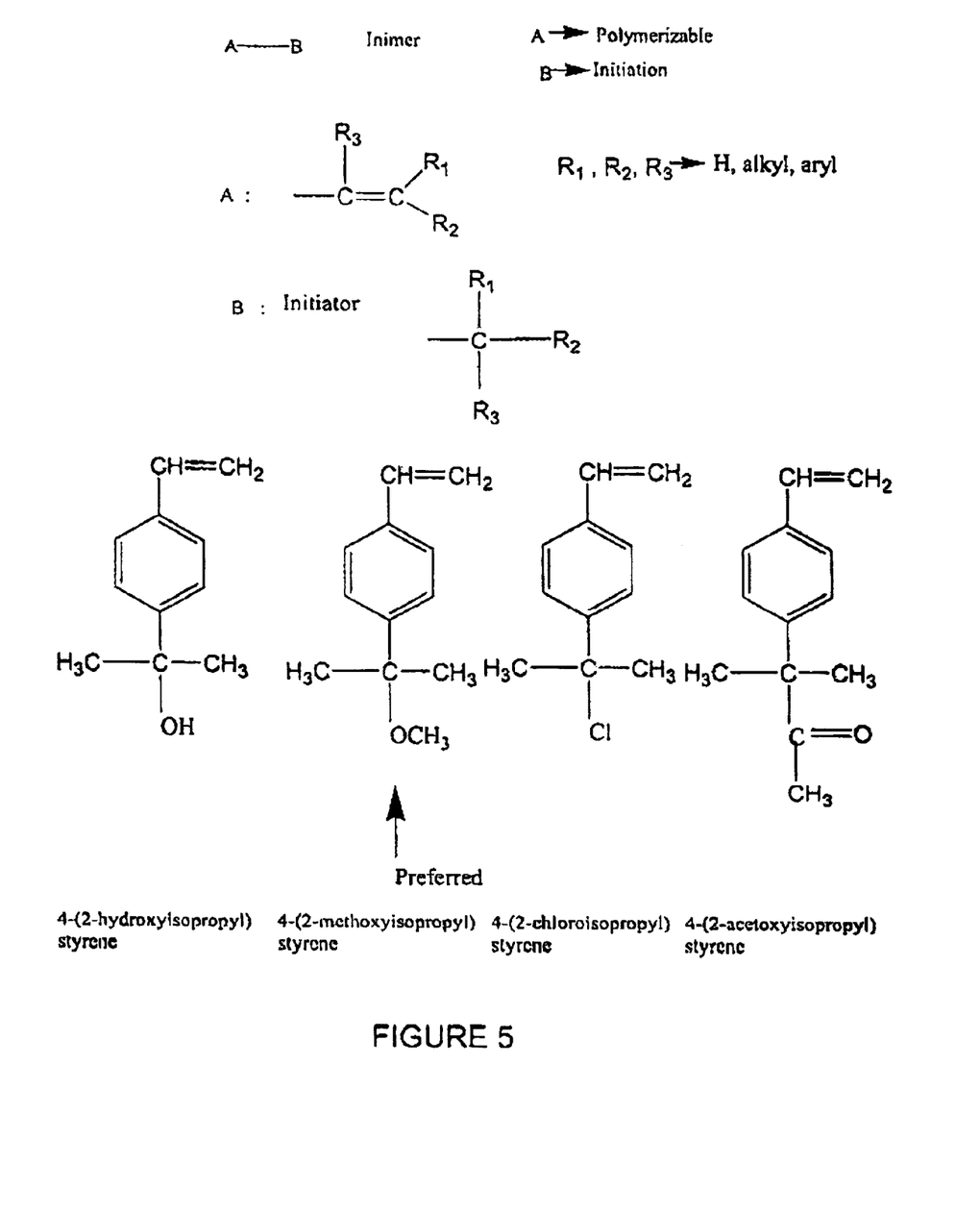
FIG. 5 shows several examples of inimers which may be used in the process shown in FIG. 3 to obtain arborescent copolymers.

FIG. 5 shows the formulas for several different inimers that may be used in the synthesis process of FIG. 3. These include 4-(2-hydroxyisopropyl)styrene; 4-(2-methoxyisopropyl)styrene; 4-(2-chloroisopropyl)styrene; 4-(2-acetoxyisopropyl)styrene; 2,3,5,6-tertamethyl-4-(2-hydoxy isopropyl)styrene; 3-(2-methoxyisopropyl)styrene; 4-(epoxyisopropyl)styrene; 4,4,6-trimethyl-6-hydroxyl-1-heptene; 4,4,6-trimethyl-6-chloro-1-heptene; 4,4,6-trimethyl-6,7-epoxy-1-heptene; 4,4,6,6,8-pentamethyl-8-hydroxyl-1-nonene, 4,4,6,6,8-pentamethyl-8-chloro-1-nonene; 4,4,6,6,8-pentamethyl-8,9-epoxy-1-nonene; 3,3,5-trimethyl-5-hydroxyl-1-hexene; 3,3,5-trimethyl-5-chloro-1-hexene; 3,3,5-trimethyl-5-6-epoxy-1-hexene; 3,3,5,5,7-pentamethyl-7-hydroxyl-1-octene, 3,3,5,5,7-pentamethyl-7-chloro-1-octene; 3,3,5,5,7-pentamethyl-7,8-epoxy-1-octene.

If the initiator function B shown in FIG. 3 is an oxirane ring, so that the initiator has the formula where R can be H, $CH_3$ or an alkyl or aryl group, then each branching point has a hydroxy group incorporated Into the polystyrene elastomeric block, as described in J. Song, J. Bodis and J. E. Puskas: Direct Functionalization of Polyisobutylene by Living Initiation with α-Methylstyrene Epoxide. J. Polym. Sci., Polym. Chem. 40(8), 1005–1015 (2002). This very advantageously increases the hydrophilicity of the rubbery segments, which is very important and useful in biomedical applications.

The isoolefins which are used in the synthesis of the highly branched polyisoolefin are those with the formula where R represents a $C_1$ to $C_4$ alkyl group such as methyl, ethyl or propyl. Isobutylene and 2-methyl-1-butene are preferred, and isobutylene is particularly preferred.

Monovinylidene arenes suitable for the production of the polyvinylidene blocks that form endblocks on some of the branches of the highly branched polyisoolefin are selected from the group consisting of $C_8$ to $C_{12}$ monovinylidene arenes which may be substituted with a $C_1$ to $C_{12}$ alkyl or alkoxy group or a fluorine, chlorine, bromine or iodine atom on the aromatic ring. Preferred monovinylidene arenes are selected from the group consisting of styrene, p-methylstyrene, p-tertiarybutylstyrene, p-chlorostyrene, indene and mixtures thereof. Particularly preferred is styrene.

The highly branched polyisoolefin that is used as a basis for producing the highly branched block copolymers of the present invention have a branching frequency of from about 5 to about 60, preferably of from about 8 to about 35.

In order that the highly branched block copolymers of the present invention exhibit thermoplastic elastomeric properties it is preferred that the weight percent of the polymonovinylidene arene endblocks in the block copolymers be of from about 5 to about 50 weight percent.

The number average molecular weight, $M_n$, of the highly branched polyisolefins is from about 10,000 to about 2,000,000, preferably from about 500,000 to about 1,000,000. The molecular weight distribution of the highly branched polyisoolefin is from about 1 to about 20, preferably from about 1.2 to about 2.8.

The process according to the present invention is carried out in an inert organic solvent or solvent mixture in order that the highly branched polyisoolefin and the final block copolymer remain in solution and at the same time there is some degree of polarity so that the polymerization proceeds at a reasonable rate. In order to fulfil these requirements a single solvent that may be used is n-butyl chloride or a mixture of a nonpolar solvent and a polar solvent wherein suitable nonpolar solvents include methylcyclohexane and cyclohexane and appropriate polar solvents include ethyl chloride, methyl chloride and methylene chloride. Especially preferred is a mixture of methylcyclohexane and methyl chloride. To achieve suitable solubility and polarity it has been found that the ratio of the nonpolar solvent to the polar solvent on a weight basis should be from about 80:20 to about 40:60, preferably about 60:40.

The temperature range within which the process is carried out is from about −20 to −100° C., preferably from about −50 to −80° C. The procedure of the present invention is preferably carried out using a 1 to 30 percent polyisoolefin solution (weight/weight basis), especially between 5 and 10 weight percent.

In order to produce the highly branched block copolymers of the present invention it is necessary to employ a coinitiator, a Lewis acid halide. Suitable Lewis acid halides include boron trichloride, aluminum trichloride and titanium tetrachloride, titanium tetrachloride being preferred. The ratio of the initiator to the monovinylidene arene on a molar basis is from about 1:1 to about 1:30, preferably from about 1:10 to about 1:20.

The highly branched block copolymers of the present invention may also be produced in a one-step process wherein the isoolefin is copolymerized with the initiator monomer in conjunction with the coinitiator in a solution at a temperature of from about −20 to −100° C. An electron donor and a proton trap are then introduced, followed by the addition of a pre-chilled solution of the monovinylidene arene in the solvent and the polymerization is allowed to continue until it is terminated by the addition of a prechilled nucleophile such as methanol. The polymerization reaction is allowed to proceed for a preselected period of time prior to being terminated in order to produce the arborescent branched block copolymer structure as shown in FIG. 4.

Alternatively, in order to connect two or more of the arborescent structures shown in FIG. 4, the polymerization process is allowed to continue after all the styrene is consumed, as disclosed in U.S. Pat. No. 5,721,331 issued to Shachi et a., which is incorporated herein by reference. This patent discloses that when the polymerization process is continued after the styrene monomer is consumed, the active living chain ends can attack the styrene block of another chain, creating multiblocks with each block being one of the arborescent blocks shown in FIG. 4. The individual arborescent branched block copolymers are bound together wherein at least one of the polymonovinylidene arene plastic endblocks on one arborescent branched block copolymer is chemically bound to one polymonovinylidene arene plastic endblock on another arborescent branched block copolymer. Thus when multiblocks are the desired end product, the polymerization reaction is allowed to proceed for a longer period of time prior to terminating the polymerization reaction by addition of a suitable nucleophile.

The production of the highly branched block copolymers necessitates the use of additives such as electron pair donors to improve blocking efficiency and proton traps to minimize homopolymerization. Examples of suitable electron pair donors are those nucleophiles that have an electron donor number of at least 15 and no more than 50 as tabulated by Viktor Gutmann in "The Donor Acceptor Approach to Molecular Interactions", Plenum Press(1978) and include ethyl acetate, dimethylacetamide, dimethylformamide and dimethyl sulphoxide, dimethyl acetamide being preferred. Suitable proton traps include 2,6-ditertiarybutylpyridine, 4-methyl-2,6-ditertiarybutylpyridine and diisopropylethylamine, 2,6-ditertiarybutylpyridine being preferred.

While not wishing to be bound by any theory it is believed that the degree of branching of the polyisoolefin, the molecular weight distribution of the polyisoolefin, the weight ratio of the coinitiator to the polyisoolefin, the molar ratio of the coinitiator to the monovinylidene arene, the reaction temperature and the reaction time may affect the extent to which endblocking of the polyisoolefin branches occurs. As a consequence by varying some of the aforementioned parameters it is possible to produce highly branched block copolymers with different thermoplastic elastomeric properties.

EXAMPLES

The highly branched polyolefins that are the basis for the production of the highly branched block copolymers of the present invention were prepared using the general procedure outlined above. The polymerizations were carried out under a dry nitrogen atmosphere in a Mbraun Labmaster 130 glove box maintained at a temperature of −80° C. with an FTS Flexi Cool Immersion Cooler. A 3-necked round bottom flask of an appropriate size, equipped with an overhead stirrer was charged with a mixture of methylcyclohexane and methyl chloride 60/40 (v/v) and then in sequence was added the initiator-monomer, 4-(2-methoxy) isopropylstyrene, the proton trap 2,6-ditertiarybutylpyridine, and the isoolefin, in this instance isobutylene. Polymerization was then begun by the rapid addition of a chilled stock solution of the coinitiator, titanium tetrachloride in methylcyclohexane. Upon completion the reaction was quenched by the addition of prechilled methanol. The polymer was isolated and purified in the usual manner and dried in a vacuum oven for one week.

The block polymers of the present invention were characterized in the following manner. The polymer Mns, Mws, and MWDs were determined by Size Exclusion Chromatography using a Waters system equipped with six Styragel columns (106, 105, 104, 103, 500 and 100 A pore sizes). A Waters 410 DRI detector, a Dawn DSP 18 angle Laser Light Scattering detector and a Waters 996 PDA detector. The elution medium, tetrahydrofuran, maintained at a temperature of 35° C. was pumped at a rate of 1 ml/min. Absolute MWs were obtained using Astra software. As the highly branched polyisobutylene contained less than 1 percent of the initiator monomer, the value dn/dc=0.93 from J. Wiley & Sons, Polymer Handbook 3rd Edition, was used for the calculations. In the case of the highly branched block copolymers of polyisobutylene and polystyrene the formula dn/dc (block)=(wt % styrene)×dn/dc(styrene)+(wt % PIB)× dn/dc(PIB). These methods gave good agreement with data obtained by assuming 100% mass recovery on the SEC columns. 1H NMRs were conducted using a Varian Gemini 300 MHz NMR with deuterated chloroform as solvent.

The branching frequencies of the polyisobutylenes were determined by the selective destruction of the branching points using a procedure based on that reported by Kennedy et al. in Polymer Bulletin, 1981, in which the aromatic core of a three-arm star branched polymer is selectively destroyed without affecting the polymer chains. From the ratios of the number average molecular weights before and after link destruction the branching frequencies were then calculated. The following examples are intended to illustrate the embodiments of the invention and are not intended to limit the scope of the invention.

Table 1 lists the molecular weight and branching frequency data for the highly branched polyisobutylenes used in the examples.

TABLE 1

| Sample ID | $M_n$ g/mol | $M_w$ g/mol | MWD | Branching frequency |
|---|---|---|---|---|
| PIB 1 | 561,000 | 681,000 | 1.2 | 33.0 |
| PIB 2 | 392,000 | 1,039,000 | 2.6 | 11.6 |

[1]Branching frequency determined experimentally

Example 1

The inimers used are listed in Table 1. The arborescent polyisobutylenes listed in Table 1 were produced with 4-(2-methoxy)isopropylstyrene as an inimer. In a Mbraun Labmaster 130 glove box under an atmosphere of nitrogen a 3-necked flask equipped with an overhead stirrer was charged with a mixture of methylcyclohexane and methyl chloride and cooled to a temperature of −80° C. by means of a FTS Flexi Cool Immersion Cooler. To this solution there was then added 0.196 g (1.024 mmol) 2,6-ditertiarybutylpyridine, 0.08 g (0.968 mmol) N,N-dimethylacetamide and 5 g (0.048 mol) styrene. To this solution was added 10 g PIB 1 which had been dissolved overnight in 100 ml of methylcyclohexane affording a 2.5 weight percent solution of the PIB 1 in 200 ml of a 60/40 (w/w) mixture of methylcyclohexane and methyl chloride. The reaction mixture was thoroughly stirred and polymerization was initiated by the addition of 2.02 g (0.011 mol) of titanium tetrachloride. After approximately 50 minutes stirring the reaction was terminated by the addition of prechilled methanol. Analysis by Size Exclusion Chromatography revealed that in addition to the polyisobutylene-polystyrene block copolymer there was a significant amount of homopolystyrene present, necessitating that the total product be washed with methyl ethyl ketone three times and then dried. $^1$H NMR spectroscopic analysis revealed that the amount of polystyrene in the block copolymer was 9.4 weight percent. The Mn of the block copolymer PIB 1-PSty was 595,400 g/mol and the $M_w/M_n$ was 1.3 as measured by Size Exclusion Chromatography coupled with Multiangle Laser Light Scattering.

Example 2

This was performed in an analogous manner to Example 1. To a mixture of methylcyclohexane and methyl chloride maintained at a temperature of −80° C. was added 0.051 g (0.267 mmol) 2,6-ditertiarybutylpyridine, 0.12 g (1.377 mmol) N,N-dimethylacetamide and 2.5 g (0.024 mol) styrene. To this solution was added 5 g PIB 2 which had been dissolved overnight in 50 ml of methylcyclohexane affording a 2.5 weight percent solution of PIB 2 in 100 ml of a 60/40 (w/w) mixture of methylcyclohexane and methyl chloride. The reaction mixture was stirred thoroughly and the polymerization was initiated by the addition of 3.8 g (0.020 mol) of titanium tetrachloride. After approximately 60 minutes stirring the reaction was terminated by the addition of prechilled methanol. Analysis by Size Exclusion Chromatography revealed that other than the block copolymer there was very little polystyrene present. $^1$H NMR spectroscopic analysis indicated that the amount of polystyrene present in the block copolymer was 16.4 weight percent. The $M_n$ of the block copolymer PIB 2-PSty was 543,400 g/mol and the $M_w/M_n$ was 2.6 as measured by Size Exclusion Chromatography coupled with Multiangle Laser Light Scattering.

Physical Characterization

Physical characterization of the highly branched block copolymers PIB 1-PSty and PIB 2-PSty1 was carried out by compression moulding the samples (thickness~0.8 mm) at 210° C. for 3 minutes in an electrically heated hydraulic press at a pressure of 10 MPa. Prior to the pressure being applied the samples were preheated for 5 minutes. The results are shown in Table 2.

The above results clearly indicate that with the introduction of the polystyrene endbocks on to some of the entangled branches of the polyisobutylenes, the block copolymers exhibit a self-reinforcing characteristic as a result of the fact that there is phase separation between the polyisobutylene block and the polystyrene blocks. This is particularly evident in the significant increase in the tensile strengths of the block copolymers PIB 1-PSty and PIB 2-PSty relative to the tensile strengths of PIB 1 and PIB 2 respectively.

Atomic force microscopy substantiates this conclusion in that the phase contrast picture of the block copolymer PIB 2-PSty exhibits polystyrene blocks irregularly distributed amongst the polyisobutylene block.

Three further reactions were carried out using the highly branched polyisobutylene PIB 2 but varying the conditions such as the length of reaction time, the order of addition, the amount of the initiator and the amounts of the electron donor and the proton trap.

Example 3

This was performed in an analogous manner to Example 1.5 g of PIB 2 was dissolved in 128 ml of methylcyclohexane and the solution was cooled to −80° C. To this solution was then added 50 ml methyl chloride, 0.196 g (1.02 mmol) 2,6-ditertiarybutyl pyridine, 0.084 g (0.968 mmol) N,N-dimethylacetamide and 6.06 g (0.032 mol) titanium tetrachloride. Polymerization was then initiated by the addition of 5 g (0.048 mol) styrene and allowed to proceed for 16 hours, at which point it was then terminated by the addition of methanol. The resultant block copolymer PIB 2-PSty 3 was extracted with methyl ethyl ketone and dried. $^1$H NMR spectroscopic analysis of the block copolymer revealed that it contained 34 weight percent polystyrene. The $M_n$ of the final product was 585,405 g/mol and the $M_w/M_n$ was 2.7 as measured by Size Exclusion Chromatography coupled with Multiangle Laser Light Scattering.

Example 4

This reaction was performed in an analogous manner to Example 1. An amount of 5 g of PIB 2 was dissolved in 167 ml of methylcyclohexane and the solution and the solution was cooled to 80° C. To this solution was then added 101 ml of methyl chloride, 0.15 g (0.8 mmol) ditertiarybutyl pyridine, 0.07 g (0.806 mmol) N,N-dimethylacetamide and 31.2 g (0.300 mol) styrene. The polymerization was initiated by the addition of 9.11 g (0.048 mol) titanium tetrachloride. The reaction was allowed to proceed for 8 hours and then terminated by the addition of methanol. The resultant block copolymer PIB 2-PSty 4 was then extracted with methyl ethyl ketone and dried. $^1$H NMR spectroscopic analysis of the block copolymer revealed that the block copolymer contained 31 weight percent styrene. The $M_n$ of the final product was 560,000 g/mol and the $M_w/M_n$ was 2.3. The products from Examples 3 and 4 were not elastomeric like the starting PIB 2 but very strong, tough materials that extended like a crosslinked rubber and regained their shape when the stress was released. This is evident from their physical characteristics which are listed in Table 2.

Example 5

This reaction was performed in an analogous manner to Example 1. An amount of 5 g of PIB 2 was dissolved in 167 ml of methylcyclohexane and the solution and the solution was cooled to −80° C. To this solution was then added 101 ml methyl chloride, 0.290 g (1.514 mmol) ditertiarybutyl pyridine, 0.131 g (1.506 mmol) N,N-dimethylacetamide and 31.2 g (0.300 mol) styrene. The polymerization was initiated by the addition of 9.11 g (0.048 mol) titanium tetrachloride. The reaction was allowed to proceed for 8 hours and then terminated by the addition of methanol. The resultant block copolymer PIB 2-PSty 4 was then extracted with methyl ethyl ketone and dried. 1H NMR spectroscopic analysis of the block copolymer revealed that the block copolymer contained 27 weight percent styrene. The Mn of the final product was 530,000 g/mol and the Mw/Mn was 2.3.

Example 6

This example is to demonstrate that epoxy intitiation introduces a hydroxy functional group into the PIB chain. The reaction vessel in a glove box under dry nitrogen was charged with 100 ml total reaction volume containing 2.1 mol/L isobutylene (IB) monomer, 0.019 mol/L 2-methyl-2-phenyl-oxirane or α-Methylstyrene epoxyde (MSE) initiator, 0.007 mol/L 2,6-di-(tertiary-butyl)-pyridine proton trap and methylcyclohexane/methyl chloride 60/40 volume/volume solvent mixture, cooled to −60° C. The reaction was started with the addition of 0.064 mol/L prechilled TiCl4. The reaction was terminated after 10 minutes by prechilled methanol. 2.4 g polymer was recovered. The molecular weight of the polymer was Mn=4346 g/mol with Mw/Mn= 1.07. The hydroxy functionality was determined by FTIR using 2-phenylpropanol to create a calibration curve: functionality Fn=1.1 was found. The hydroxy group was reacted with trimethylchlorosilane as described 25 and the functionality was determined by 1H NMR. Fn=1.03 was found.

The products from Examples 3, 4 and 5 were not elastomeric like the starting PIB 2 but very strong, tough materials that extended like a crosslinked rubber and regained their shape when the stress was released. This is evident from their physical characteristics which are listed in Table 2.

Surprisingly, these arborescent blocks displayed thermoplastic elastomeric properties, as evidenced by the results summarized in Table 2 which shows these arborescent TPEs display remarkable tensile strength and elongation values. For comparison, the semicommercial Kuraray sample, most likely produced by the process disclosed in U.S. Pat. No. 5,721,331 issued to Shachi et al., displayed 10 MPa tensile strength with 600% elongation at $M_n$=60,000 g/mol and 30 wt % PS content.

In addition to the superior elastomeric properties summarized in Table 2, an advantage of the method of producing the arborescent block copolymer structures disclosed herein over the multiarm-star structures is that multifunctional initiators as used to produce the latter (see S. Jacob, J. P. Kennedy, *Advances in Polym. Sci*, 146, 1 (1999)) are difficult to make and they are very expensive. Making the multiarm structures by coupling living chains (U.S. Pat. Nos. 5,428,111 and 5,458,796), is a very slow process, and can take up to 100 hours due to the high viscosity, and the number of arms is undefined. In contrast, it is very easy to make high molecular weight arborescent polyisobutylene block copolymers disclosed herein. They also exhibit better tensile strength and greater elongation in spite of the irregular structure.

The arborescent branched block copolymers disclosed herein characterized by having thermoplastic elastomeric properties are very useful for many applications and of particular interest as materials for medical devices or prostheses having resistance to cracking and fissuring after implantation. Other uses and applications will be evident to those skilled in the art where materials having combined thermoplastic elastomeric properties are needed, including gaskets, seals and the like.

As used herein, the terms "comprises" and "comprising" are to be construed as being inclusive and open ended, and not exclusive. Specifically, when used in this specification including claims, the terms "comprises" and "comprising" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

TABLE 2

| PROPERTIES | PIB 1-Psty 1 | PIB 2-Psty 2 | PIB 2-Psty 3 | PIB 2-Psty 4 | PIB 2-Psty 5 |
| --- | --- | --- | --- | --- | --- |
| 100% Modulus (MPa) | 0.42 | 0.62 | 0.70 | 0.64 | 0.28 |
| 200% Modulus (MPa) | 0.53 | 0.76 | 0.89 | 0.79 | 0.32 |
| 300% Modulus (MPa) | 0.58 | 0.88 | 1.14 | 1.02 | 0.37 |
| Tensile strength (Mpa) | 4.0 (PIB 1 0.13) | 7.3 (PIB 2 0.15) | 9.0 (PIB 2 0.15) | 7.0 (PIB 2 0.15) | 3.6 (PIB 2 0.15) |
| Elongation at break (%) | 1830 | 1150 | 950 | 980 | 1380 |
| Hardness (ShoreA) | 27 | 34 | — | — | — |

What is claimed is:

1. An arborescent branched block copolymer, comprising:
an arborescent elastomeric polymer block having more than one branching point, the arborescent elastomeric polymer block having a low glass-transition temperature ($T_g$), and some or all of the branches of the arborescent elastomeric polymer block being terminated in rigid polymer block segments with a high $T_g$ or crystalline melting point, the arborescent branched block copolymer exhibiting thermoplastic elastomeric properties.

2. The arborescent branched block copolymer according to claim 1 wherein said arborescent elastomeric polymer block with a low glass-transition temperature ($T_g$) includes an arborescent polyisoolefin block, wherein said rigid polymer block segments with a high $T_g$ or crystalline melting point include polymonovinylidene arene plastic endblocks, and wherein some of the branches of the aforesaid arborescent polyisoolefin block terminate in said polymonovinylidene arene plastic endblocks.

3. The arborescent branched block copolymer of claim 2 wherein the total weight percent of the polymonovinylidene arene plastic endblocks is from about 5 weight percent to about 95 weight percent.

4. The arborescent branched block copolymer of claim 3 wherein said polymonovinylidene arene plastic endblocks are styrene plastic endblocks.

5. The arborescent branched block copolymer according to claim 1 wherein the arborescent branched block copolymer exhibits thermoplastic elastomeric properties.

6. An arborescent branched block copolymer of a polyisoolefin and a polymonovinylidene arene comprising an arborescent elastomeric polyisoolefin polymer block having more than one branching point, and some or all of the branches of the aforesaid arborescent polyisoolefin polymer block terminate in polymonovinylidene arene plastic endblocks, the arborescent branched block copolymer having thermoplastic elastomeric properties.

7. The arborescent branched block copolymer of claim 6 wherein the polyisoolefin comprises an isoolefin having the formula wherein R is a $C_1$–$C_4$ alkyl group.

8. The arborescent branched block copolymer of claim 7 wherein the isoolefin is selected from the group of isobutylene and 2-methyl-1-butene.

9. The arborescent branched block copolymer of claim 8 wherein the isoolefin is isobutylene.

10. The arborescent branched block copolymer of claim 6 wherein the polymonovinylidene arene comprises a monovinylidene arene selected from the group consisting of $C_8$ to $C_{12}$ monovinylidene arenes which may be substituted with a $C_1$ to $C_4$ alkyl group or alkoxy group or a chlorine or bromine atom on the aromatic ring.

11. The arborescent branched block copolymer of claim 10 wherein the monovinylidene arene is selected from the group consisting of styrene, p-methylstyrene, p-ditertiarybutylstyrene, p-methoxistyrene, p-chlorostyrene and mixtures thereof.

12. The arborescent branched block copolymer of claim 10 wherein the monovinylidene arene is styrene.

13. The arborescent branched block copolymer of claim 6 wherein the arborescent polyisoolefin polymer block has a branching frequency of from about 5 to about 60.

14. The arborescent branched block copolymer of claim 12 wherein the arborescent polyisoolefin polymer block has a branching frequency of from about 8 to about 35.

15. The arborescent branched block copolymer of claims 6 wherein the total weight percent of the polymonovinylidene arene endblocks is from about 5 to about 50 weight percent.

16. The arborescent branched block copolymer of claim 6 wherein the number average molecular weight of the arborescent polyisoolefin polymer block is from about 10,000 to about 2,000,000.

17. The arborescent branched block copolymer of claim 16 wherein the number average molecular weight of the arborescent polyisoolefin polymer block is from about 15,000 to about 2,500,000.

18. The arborescent branched block copolymer of claim 6 wherein the molecular weight distribution (MWD) of the arborescent polyisoolefin polymer block is in a range 1<MWD≦20.

19. The arborescent branched block copolymer of claim 18 wherein the molecular weight distribution of the highly branched polyisoolefin block is from about 1.2 to about 2.8.

20. An arborescent branched block copolymer of polyisobutylene and polystyrene comprising an arborescent elastomeric polyisobutylene polymer block having more than one branching point and some or all of the branches of the aforesaid arborescent polyisobutylene polymer block being terminated with polystyrene endblocks, the arborescent branched block copolymer having thermoplastic elastomeric properties.

21. The arborescent branched block copolymer of claim 20 wherein said arborescent polyisobutylene polymer block has a branching frequency of from about 8 to about 35.

22. The arborescent branched block copolymer of claim 20 wherein the total weight percent of the polystyrene endblocks is from about 5 to about 50 weight percent.

23. The arborescent branched block copolymer claim 20 wherein the molecular weight distribution of the arborescent polyisobutylene is from about 1.1 to about 20.

24. The arborescent branched block copolymer of claim 6 wherein said arborescent branched block copolymer is a first arborescent branched block copolymer, including at least two arborescent branched block copolymers connected together wherein at least one of said polymonovinylidene arene plastic endblocks on one of said at least two arborescent branched block copolymers is chemically bound to one polymonovinylidene arene plastic endblock on the other of said at least two arborescent branched block copolymers.

25. A process for producing an arborescent branched block copolymer of a polyisoolefin and a polymonovinylidene arene, comprising:

a) polymerizing an isoolefin in the presence of at least one inimer and a Lewis acid halide coinitiator, at a temperature of between about −20° C. and −100° C. to produce an arborescent elastomeric branched polyisoolefin polymer having more than one branching point, the inimer including at least one group for (co)polymerizing in a cationic polymerization of the isoolefin and at least one group for initiating cationic polymerization of the isoolefin; and thereafter b) adding a compound having an effective electron pair donor for improving blocking efficiency and adding a monovinylidene arene suitable for the production of the polyvinylidene plastic blocks with some or all of the branches of the aforesaid arborescent elastomeric branched polyisoolefin polymer being terminated with polymonovinylidene arene plastic endblocks; and c) terminating said polymerization reaction after a selected period of time by addition of an effective nucleophile compound which terminates said polymerization reaction, said selected period of time being sufficiently long enough to ensure production of at least individual units of said arborescent branched block copolymer the arborescent branched block copolymer of a polyisoolefin and a polymonovinylidene arene having thermoplastic elastomeric properties.

26. The process according to claim 25 wherein said selected period of time is sufficiently long so that multiple arborescent branched block copolymers are bound together wherein at least one of said polymonovinylidene arene plastic endblocks on one arborescent branched block copolymer is chemically bound to one polymonovinylidene arene plastic endblock on another arborescent branched block copolymer.

27. The process according to claim 25 wherein said nucleophile compound is selected from the group consisting of methanol, ethanol, isopropanol and water.

28. The process according to claim 25 wherein said monovinylidene arenes that polymerize to form the polyvinylidene blocks that form endblocks on some of the branches of the highly branched polyisoolefin are selected from the group consisting of $C_8$ to $C_{12}$ monovinylidene arenes which may be substituted with a $C_1$ to $C_4$ alkyl group or alkoxy group or a fluorine, chlorine, bromine or iodine atom on the aromatic ring.

29. The process according to claim 25 wherein said monovinylidene arenes that polymerize to form the polyvinylidene blocks that form endblocks on some of the branches of the highly branched polyisoolefin are selected from the group consisting of styrene, p-methylstyrene, p-tertiarybutylstyrene, p-chlorostyrene, indene and mixtures thereof.

30. The process according to claim 25 wherein said isoolefin used in the synthesis of the highly branched polyisoolefin has a formula where R represents a $C_1$ to $C_4$ alkyl group selected from the group consisting of methyl, ethyl and propyl groups.

31. The process according to claim 29 wherein the isoolefin is selected from the group of isobutylene and 2-methyl-1-butene.

32. The process according to claim 31 wherein the isoolefin is isobutylene.

33. The process according to claim 25 wherein said at least one inimer is selected from the group consisting of 4-(2-hydroxy-isopropyl) styrene and 4-(2-methoxy-isopropyl) styrene.

34. The process according to claim 25 wherein said at least one inimer is selected from the group consisting of 4-(2-hydroxyisopropyl)styrene; 4-(2-methoxyisopropyl) styrene; 4-(2-chloroisopropyl)styrene; 4-(2-acetoxyisopropyl)styrene; 2,3,5,6-tertamethyl-4-(2-hydoxy isopropyl)styrene; 3-(2-methoxyisopropyl)styrene; 4-(epoxyisopropyl)styrene; 4,4,6-trimethyl-6-hydroxyl-1-heptene; 4,4,6-trimethyl-6-chloro-1-heptene; 4,4,6-trimethyl-6,7-epoxy-1-heptene; 4,4,6,6,8-pentamethyl-8-hydroxyl-1-nonene, 4,4,6,6,8-pentamethyl-8-chloro-1-nonene; 4,4,6,6,8-pentamethyl-8,9-epoxy-1-nonene; 3,3,5-trimethyl-5-hydroxyl-1-hexene; 3,3,5-trimethyl-5-chloro-1-hexene; 3,3,5-trimethyl-5-6-epoxy-1-hexene; 3,3,5,5,7-pentamethyl-7-hydroxyl-1-octene, 3,3,5,5,7-pentamethyl-7-chloro-1-octene; 3,3,5,5,7-pentamethyl-7,8-epoxy-1-octene.

35. The process according to claim 25 wherein said compound having an electron pair donor includes moieties which function as proton traps for reducing homopolymerization.

36. The process according to claim 25 wherein said compound having an electron pair donor includes nucleophiles that have an electron donor number of at least 15.

37. The process according to claim 36 wherein said compound compound having an electron pair donor is selected from the group consisting of ethyl acetate, dimethylacetamide, dimethylformamide, dimethyl sulphoxide and dimethyl acetamide.

38. The process according to claim 35 wherein said compound having an electron pair donor which include moieties which function as proton traps are selected from the group consisting of 2,6-ditertiarybutylpyridine, 4-methyl-2, 6-ditertiarybutylpyridine and diisopropylethylamine, pyridine, and 2,6-dimethypyridine.

39. The process according to claim 25 wherein said Lewis acid halide coinitiator is selected from the group consisting of boron trichloride, aluminum trichloride and titanium tetrachloride.

40. The process according to claim 25 wherein said Lewis acid halide coinitiator is titanium tetrachloride.

41. The process according to claim 25 wherein said at least one inimer is a compound having a formula A-R1-B, where R1 can be an aliphatic and aromatic moiety, A is a vinyl group that can be polymerized under cationic condition, wherein B is an oxirane ring so that each branching point of the polyisobutylene elastomeric blocks includes a hydroxy group attached thereto.

42. The process according to claim 25 wherein the isoolefin is polymerized in the presence of one or more inert, organic solvents.

43. The process according to claim 42 wherein the one or more inert, organic solvents is a mixture of a nonpolar organic solvent and a polar organic solvent.

44. The process according to claim 43 wherein said nonpolar organic solvent is selected from the group consisting of hexane, methylcyclohexane, cylopentane and cyclohexane.

45. The process according to claim 43 wherein said polar organic solvent is selected from the group consisting of n-butylchloride, ethyl chloride, methyl chloride and methylene chloride.

46. The process according to claim 43 wherein the one or more inert, organic solvents is a mixture of methylcyclohexane and methyl chloride.

47. The process according to claim 43 wherein said mixture of a nonpolar organic solvent and a polar organic solvent has a ratio of the nonpolar solvent to the polar solvent on a weight basis from about 80:20 to about 40:60, preferably about 60:40.

48. The process according to claim 47 wherein said ratio of the nonpolar solvent to the polar solvent on a weight basis is about 60:40.

49. The process according to claim 48 wherein a ratio of the coinitiator to the monovinylidene arene on a molar basis is from about 1:1 to about 1:30, preferably from about 1:10 to about 1:20.

50. The process according to claim 49 wherein the ratio of the coinitiator to the monovinylidene arene on a molar basis is from about 1:10 to about 1:20.

51. A process for producing an arborescent branched polyisoolefin block copolymer, comprising:
a) polymerizing an isoolefin in the presence of an inimer and a Lewis acid halide coinitiator at a temperature of between about –20° C. and –100° C. to produce an elastomeric arborescent branched polyisoolefin polymer having more than one branching point, the the inimer having a formula where R can be H, $CH_3$ or an alkyl or aryl group; thereafter
  b) adding a compound having an effective electron pair donor for improving blocking efficiency and adding a monovinylidene arene suitable for the production of the polyvinylidene arene plastic endblocks; and
  C) terminating said polymerization reaction after a selected period of time by addition of an effective nucleophile compound which terminates said polymerization reaction, said selected period of time being sufficiently long enough to ensure production of at least individual units of said elastomeric arborescent branched block copolymer with some or all of the branches of the aforesaid elastomeric arborescent polyisoolefin polymer block terminated in polymonovinylidene arene plastic endblocks, the arborescent branched block copolymer having thermoplastic elastomeric properties.

52. The process according to claim 51 wherein said selected period of time is sufficiently long so that multiple arborescent branched block copolymers are bound together wherein at least one of said polymonovinylidene arene plastic endblocks on one arborescent branched block copolymer is chemically bound to one polymonovinylidene arene plastic endblock on another arborescent branched block copolymer.

53. The process according to claim 51 wherein said Lewis acid halide coinitiator is selected from the group consisting of boron trichloride, aluminum trichloride and titanium tetrachloride.

54. The process according to claim 51 wherein said Lewis acid halide coinitiator is titanium tetrachloride.

55. The process according to claim 51 wherein said isoolefin used in the synthesis of the highly branched polyisoolefin has a formula where R represents a $C_1$ to $C_4$ alkyl group selected from the group consisting of methyl, ethyl and propyl.

56. The process according to claim 55 wherein said $C_1$ to $C_4$ alkyl group is selected from the group consisting of isobutylene and 2-methyl-1-butene.

57. The process according to claim 51 wherein the isoolefin is isobutylene.

58. The process according to claim 55 wherein the isoolefin is isobutylene.

59. The process according to claim 51 wherein said at least one multifunctional monomer is selected from the group consisting of 4-(2-hydroxy-isopropyl) styrene and 4-(2-methoxy-isopropyl) styrene.

60. The process according to claim 57 wherein the isoolefin is polymerized in the presence of one or more inert, organic solvents.

61. The process according to claim 60 wherein the one or more inert, organic solvents is a mixture of a nonpolar organic solvent and a polar organic solvent.

62. The process according to claim 61 wherein said nonpolar organic solvent is selected from the group consisting of methylcyclohexane and cyclohexane.

63. The process according to claim 61 wherein said polar organic solvent is selected from the group consisting of ethyl chloride, methyl chloride and methylene chloride.

64. The process according to claim 60 wherein the one or more inert, organic solvents is a mixture of methylcyclohexane and methyl chloride.

65. The process according to claim 61 wherein said mixture of a nonpolar organic solvent and a polar organic solvent has a ratio of the nonpolar solvent to the polar solvent on a weight basis from about 80:20 to about 40:60, preferably about 60:40.

66. The process according to claim 65 wherein said ratio of the nonpolar solvent to the polar solvent on a weight basis is about 60:40.

67. An arborescent branched block copolymer according to claim 1 formed into an article of manufacture comprising an implantable prosthesis or implant.

68. The article of manufacture of claim 67 wherein the polyisoolefin comprises an isoolefin having the formula wherein R is a $C_1$–$C_4$ alkyl group.

69. The article of manufacture of claim 68 wherein the isoolefin is selected from the group of isobutylene and 2-methyl-1-butene.

70. The article of manufacture of claim 69 wherein the isoolefin is isobutylene.

71. The article of manufacture of claim 67 wherein said article is constructed as an endoluminal or vascular device for in vivo implant.

72. The article of manufacture of claim 69 wherein said article is constructed as an endoluminal or vascular device for in viva implant.

* * * * *